United States Patent
Jinks et al.

(10) Patent No.: US 9,694,149 B2
(45) Date of Patent: Jul. 4, 2017

(54) MANUFACTURE OF MEDICINAL AEROSOL CANISTERS

(71) Applicant: 3M INNOVATIVE PROPERTIES COMPANY, St. Paul, MN (US)

(72) Inventors: Philip A. Jinks, Loughborough (GB); Christopher G. Blatchford, Loughborough (GB)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 278 days.

(21) Appl. No.: 14/352,113

(22) PCT Filed: Oct. 18, 2012

(86) PCT No.: PCT/US2012/060744
§ 371 (c)(1),
(2) Date: Apr. 16, 2014

(87) PCT Pub. No.: WO2013/059409
PCT Pub. Date: Apr. 25, 2013

(65) Prior Publication Data
US 2014/0299128 A1    Oct. 9, 2014

(30) Foreign Application Priority Data

Oct. 21, 2011   (GB) .................................. 1118188.0

(51) Int. Cl.
*A61M 15/00*     (2006.01)
*B65D 83/42*     (2006.01)
(Continued)

(52) U.S. Cl.
CPC ......... *A61M 15/009* (2013.01); *B65B 31/003* (2013.01); *B65D 83/303* (2013.01);
(Continued)

(58) Field of Classification Search
CPC ............ A61M 15/009; A61M 2207/00; A61M 2207/10; B65D 83/303; B65D 83/752; B65B 31/003
(Continued)

(56) References Cited

U.S. PATENT DOCUMENTS 3,545,726 A   12/1970   Heinz
5,215,209 A   6/1993   Radtke
(Continued)

FOREIGN PATENT DOCUMENTS

EP   0 372 777   6/1990
GB   837465      6/1960
(Continued)

OTHER PUBLICATIONS

Ganderton, D. et al.; "Drug Delivery to the Respiratory Tract"; publ. Ellis Horwood Ltd, Chichester, England; 1987; Cover, copyright, table of contents and pp. 89-90 (6 pgs).

*Primary Examiner* — Nicolas A Arnett

(57) ABSTRACT

The present invention relates to methods of making medicinal aerosol canisters (10), in particular metered dose canisters (10), comprising aerosol formulation comprising medicament particles suspended in liquid propellant, for example for delivery by pulmonary or nasal inhalation as well as medicinal dispensers (100) including such canisters (10), such as metered dose medicinal dispenser in particular pressurized metered dose inhalers, wherein the liquid propellant in some embodiments contains HFA 134a and/or HFA 227, and the propellant component is subjected to one or more ultrasonic probes.

19 Claims, 11 Drawing Sheets

(51) Int. Cl.
*B65B 31/00* (2006.01)
*B65D 83/30* (2006.01)
*B65D 83/14* (2006.01)
*C09K 3/30* (2006.01)

(52) U.S. Cl.
CPC .............. *B65D 83/752* (2013.01); *C09K 3/30* (2013.01); *A61M 2207/00* (2013.01); *A61M 2207/10* (2013.01); *F04C 2270/0421* (2013.01)

(58) Field of Classification Search
USPC .................... 141/3, 20, 71; 222/635; 53/470
See application file for complete search history.

(56) References Cited

U.S. PATENT DOCUMENTS

| | | | | |
|---|---|---|---|---|
| 5,275,212 | A * | 1/1994 | Moris | B65B 31/003 |
| | | | | 141/11 |
| 5,536,444 | A | 7/1996 | Hettche et al. | |
| 5,669,376 | A * | 9/1997 | Sioutas | A61M 15/009 |
| | | | | 128/200.18 |
| 5,674,472 | A * | 10/1997 | Akehurst | A61K 9/0073 |
| | | | | 222/635 |
| 6,136,294 | A | 10/2000 | Adjei et al. | |
| 6,515,030 | B1 | 2/2003 | Bechtel et al. | |
| 8,198,354 | B2 * | 6/2012 | Miller | A61K 9/008 |
| | | | | 524/300 |
| 2002/0197282 | A1 | 12/2002 | Mohseni et al. | |
| 2003/0180228 | A1 * | 9/2003 | Cripps | B65D 77/003 |
| | | | | 424/46 |
| 2004/0050960 | A1 * | 3/2004 | Godfrey | A61M 15/009 |
| | | | | 239/302 |
| 2004/0082520 | A1 * | 4/2004 | Buckton | A61K 47/26 |
| | | | | 514/25 |
| 2006/0211589 | A1 * | 9/2006 | Godfrey | B65D 83/48 |
| | | | | 510/161 |
| 2007/0009445 | A1 * | 1/2007 | Eck | A61K 9/0073 |
| | | | | 424/46 |
| 2007/0112114 | A1 * | 5/2007 | Miller | A61K 9/008 |
| | | | | 524/300 |
| 2009/0050143 | A1 * | 2/2009 | Boardman | A61M 15/009 |
| | | | | 128/200.23 |
| 2009/0168591 | A1 | 7/2009 | Wenzel et al. | |
| 2010/0199983 | A1 | 8/2010 | Jinks et al. | |
| 2011/0056089 | A1 | 3/2011 | Olsson et al. | |

FOREIGN PATENT DOCUMENTS

| | | |
|---|---|---|
| GB | 994734 | 6/1965 |
| GB | 2 263 064 | 7/1993 |
| WO | WO 91/11173 | 8/1991 |
| WO | WO 92/00107 | 1/1992 |
| WO | WO 94/21228 | 9/1994 |
| WO | WO 94/21229 | 9/1994 |
| WO | WO 95/15151 | 6/1995 |
| WO | WO 03/059317 | 7/2003 |
| WO | WO 03/059331 | 7/2003 |
| WO | WO 2011/098798 | 8/2011 |

* cited by examiner

Figure 1:
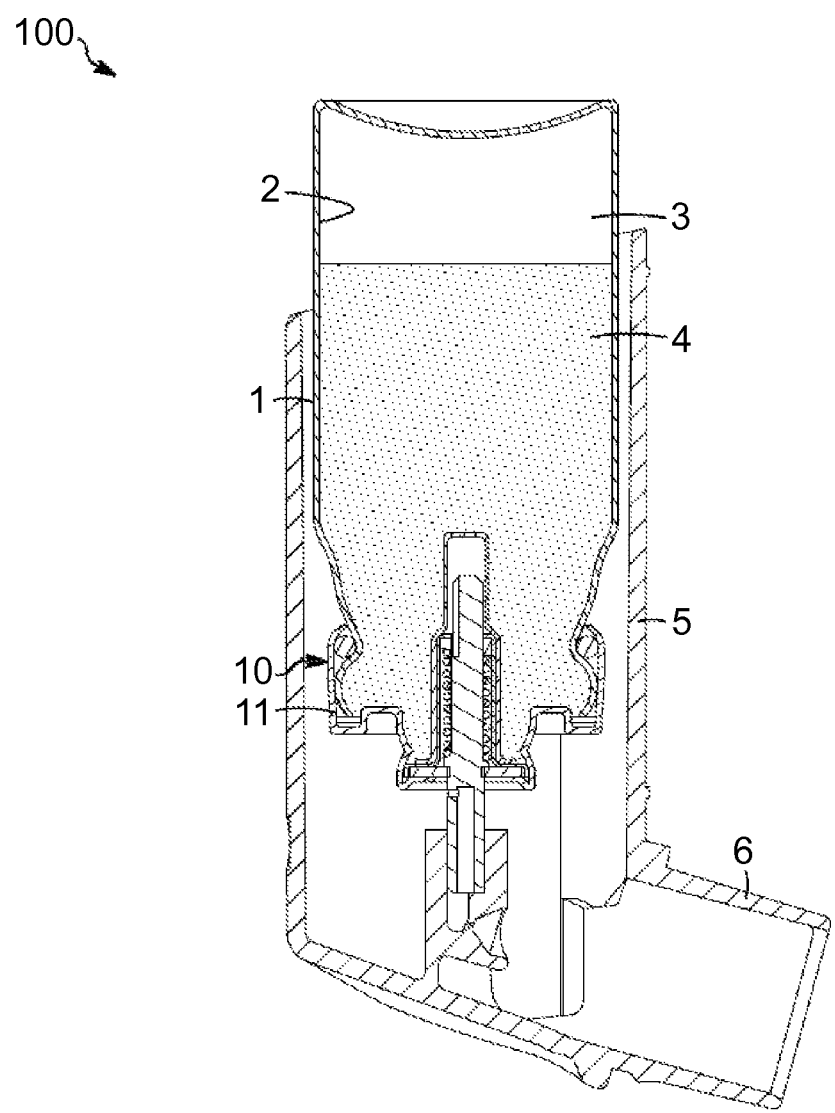
Figure 2:
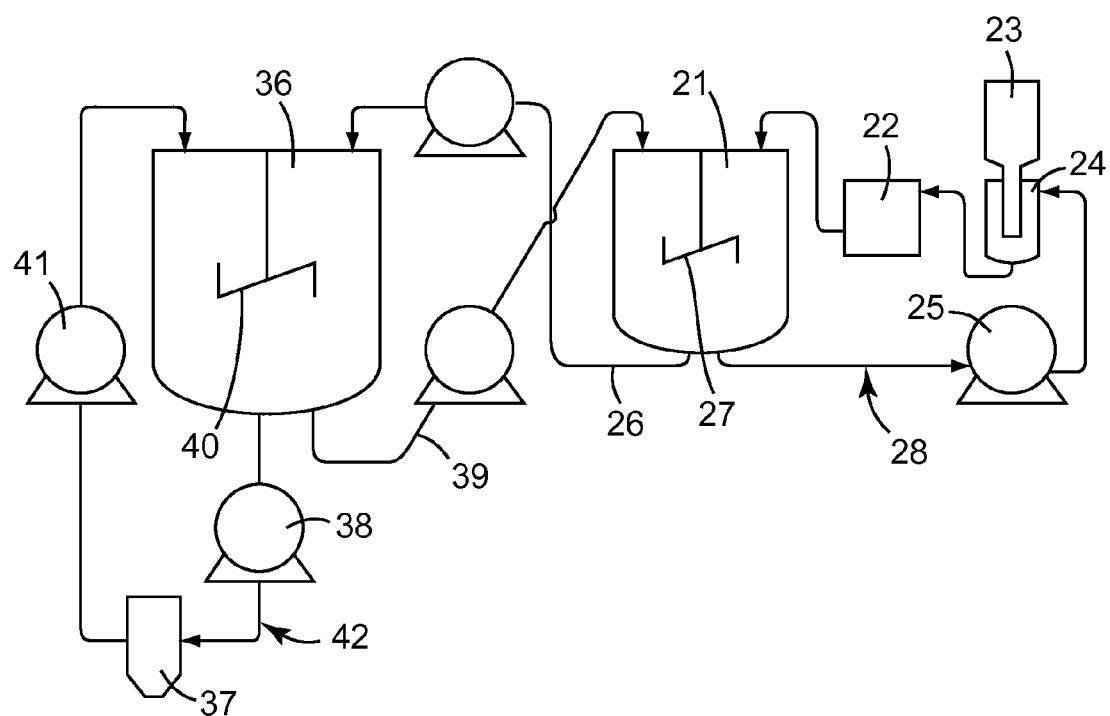
Figure 10:
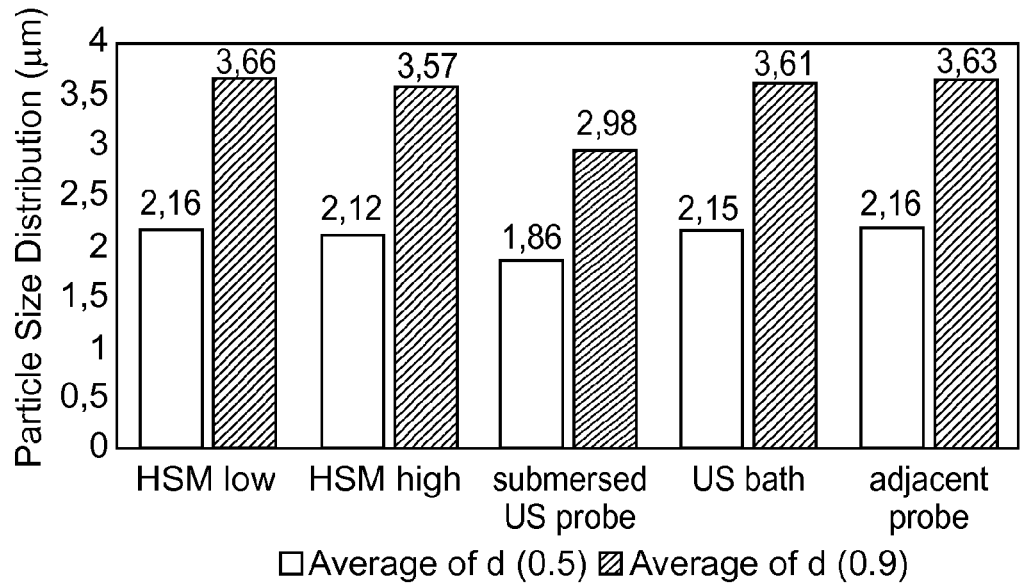

*FIG. 15a*  10 μm
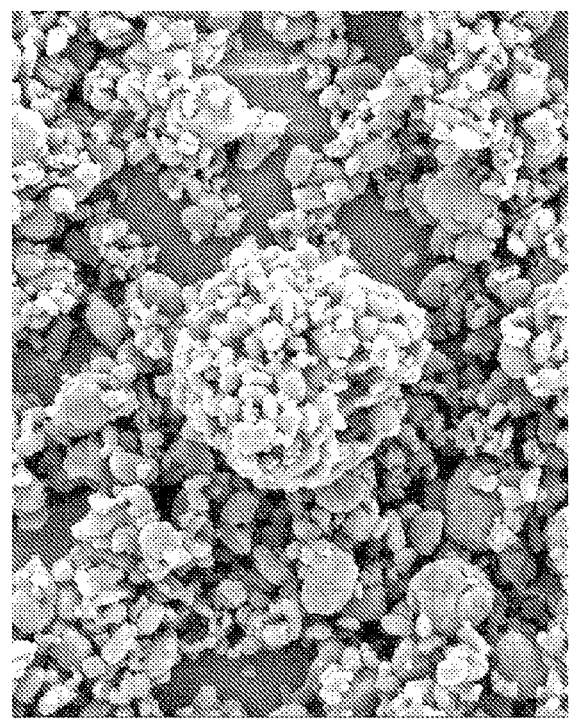
*FIG. 15b*  2 μm

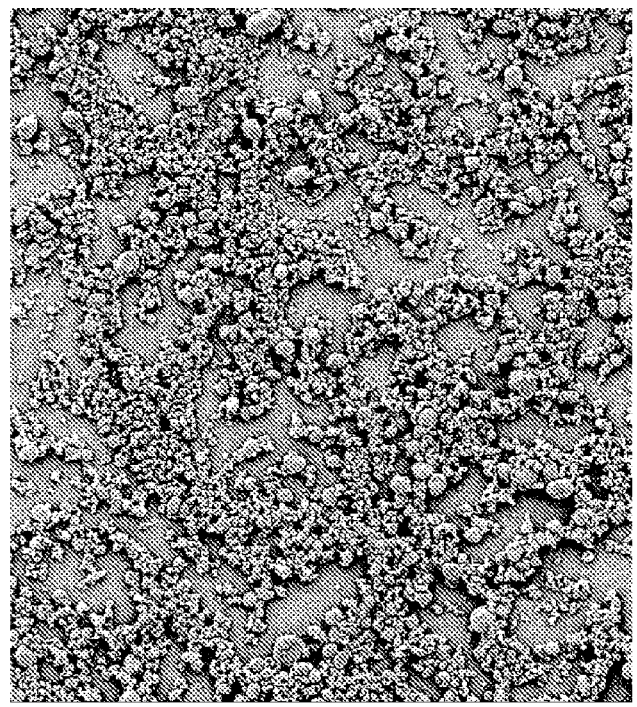
FIG. 16a  10 μm
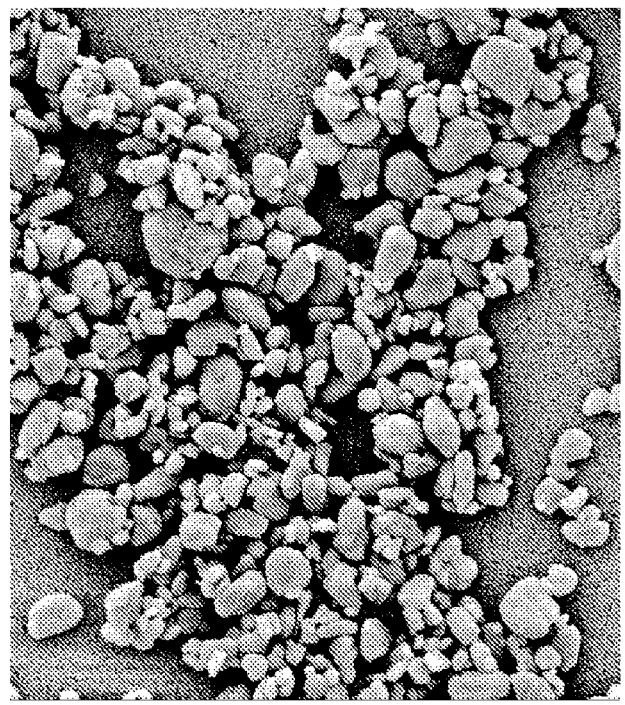
FIG. 16b  2 μm

MANUFACTURE OF MEDICINAL AEROSOL CANISTERS

CROSS REFERENCE TO RELATED APPLICATIONS

This application is a national stage filing under 35 U.S.C. 371 of PCT/US2012/060744, filed Oct. 18, 2012, which claims priority to United Kingdom Application No. GB 1118188.0, filed Oct. 21, 2011, the disclosure of which is incorporated by reference in its entirety herein.

FIELD

The present invention relates to methods of making medicinal aerosol canisters, in particular metered dose canisters, comprising aerosol formulation comprising medicament particles suspended in liquid propellant, for example for delivery by pulmonary or nasal inhalation as well as medicinal dispensers including such canisters, such as metered dose medicinal dispenser in particular pressurized metered dose inhalers.

BACKGROUND

Asthma and other respiratory diseases have long been treated by the inhalation of appropriate medicament Pulmonary inhalation is also becoming an attractive route of administration of medicaments that may be difficult to deliver orally such as proteins and peptides.

A widely used and convenient choice of pulmonary drug delivery has been the inhalation of medicament from an aerosol created by a pressurized metered dose inhaler (pMDI). pMDIs typically comprise a canister including a metered dose valve mounted on an aerosol container filled medicinal inhalation formulation and an actuator including a nasal- or mouthpiece. Suspension medicinal aerosol formulations used in canisters for pMDIs are typically prepared by dispersing, via e.g. a high shear mixer, particles of medicament in liquefied propellant(s), e.g. CFC propellant(s) and more recently non-CFC propellant(s), such as 1,1,1,2-tetrafluoroethane (HFA134a) and/or 1,1,1,2,3,3,3-heptafluoropropane (HFA227). If desired and/or deemed necessary, the formulation may comprise other components, such as excipients, co-solvents, and suspending aids.

SUMMARY OF THE INVENTION

Although pMDIs are and have been one of the main pulmonary drug delivery systems, there still are efficacy issues. The efficacious of a delivered metered amount of medicinal inhalation formulation is related in part to the respirability of the aerosol produced by the device, which is typically referred to by its respirable fraction, i.e. that fraction of medicament relative to the amount medicament in the actuated dose that reaches the lungs. Respirable fractions low as 5% are not unheard of. A number of approaches have been used to increase respirable fractions, including increasing total concentration of medicament which it is not advantageous in terms of costs due to higher costs in using higher amounts of (typically expensive) medicament and for the patient due to the fact that the patient is unnecessarily exposed to yet higher amounts of deposited medicament in the oropharyngeal region. Other approaches include using a nasal-/mouthpiece extender which is disadvantageous in that patients often shy away from using such extenders, or using a solution formulation (i.e. drug dissolved in propellant) in conjunction with a smaller nozzle orifice in the actuator which is simply not possible with most drugs due to the fact that they cannot be dissolved in a workable aerosol formulation.

There is an ongoing need to provide medicinal aerosol canisters (e.g. metered dose canisters) for e.g. medicinal aerosol dispensers (in particular metered dose dispensers, more particularly pressurized metered dose inhalers) that provide enhanced consistency in dispensing suspension medicament aerosol formulations, in particular that provide improved dose consistency and/or enhanced efficacy (e.g. respirability for pMDIs) without necessarily having to increase concentration of medicament.

We have recently discovered that during the large scale filling process to manufacture medicinal metered dose canisters filled with suspension formulation, the high shear mixing of the suspension aerosol formulation that is typically used prior to the actual filling surprisingly seems insufficient to break up agglomerates which frequently exist in the dry input, particulate active ingredient. Particulate active ingredient (drug(s)) are typically processed (e.g. micronized) by the drug producer to have a primary particle size generally having a mass median particle diameter of 5 microns or less. Often during storage and/or transport and/or due to other reasons, primary particles of the particulate active ingredient form agglomerates, and the dry powder, particulate active ingredient is in agglomerated form at the time they used to produce filled medicinal aerosol canisters. Such agglomerates are termed in the following as primary agglomerates. In general agglomerates are understood to be assemblage of particles fused or cemented together e.g. as by partial fusion, and such assemblages are difficult to separate and normally cannot be broken up during normal use of the filled canister (e.g. by the shaking of the metered dose canister by the patient). Conversely flocs formed during flocculation (a common phenomenon in suspension aerosol formulations) are generally understood to be assemblages of loosely coherent particles having much lower separation energy and easily broken up by during normal use of the filled canister (e.g. by mere shaking of the metered dose canister in a pMDI by the patient).

Moreover, it has been found that from lot to lot of active ingredient, there may significant differences in the amount and size of primary agglomerates leading to lot to lot inconsistencies in dose delivery (e.g. respirability) from the filled canisters (e.g. of pMDIs). Such inconsistency is particularly undesirable for pharmaceutical products and particularly troublesome in large scale manufacturing of medicinal aerosol canisters.

Surprisingly we have found that during large scale filling where the targeted number of canisters to be filled is greater than 500, in particular 2000 or more, more particularly 5000 or more, that by subjecting a mixture of particulate drug and liquefied HFA 134a and/or HFA 227 propellant and, optionally, other non-HFA 134a/HFA 227-propellant component or components to one or more powered ultrasonic probes (e.g. one or more elongate, powered ultrasonic probes), said one or more probes being submersed in said mixture, while agitating said mixture and while providing the mixture or after providing the mixture improves significantly dose consistency from lot to lot as well as improves dose delivery (e.g. respirable fraction, for example either in terms of significantly reducing throat deposition or increasing lung deposition).

Accordingly, one aspect of the present invention is the provision of a method of manufacturing medicinal aerosol canisters containing a medicinal formulation comprising particulate drug dispersed in liquefied HFA 134a and/or HFA 227 propellant, wherein the targeted number of canisters to be filled is greater than 500, the method comprising the steps:

(a) providing a mixture comprising a particulate drug and liquefied HFA 134a and/or HFA 227 propellant and, optionally, other non-HFA 134a/HFA 227-propellant component or components;

either simultaneously or subsequently to said step of providing (step a), (b) subjecting said mixture to one or more powered ultrasonic probes, said one or more probes being submersed in said mixture, while agitating said mixture;

subsequently to said steps of providing and subjecting (steps a and b), (c) filling treated mixture into aerosol containers followed by attaching a valve to each filled container (cold filling) or alternatively filling treated mixture into aerosol containers through a valve pre-attached onto each container (pressure filling).

Subjecting the aforesaid mixture to one or more submersed, powered ultrasonic probes (powered ultrasonic transducer(s) in part or fully beneath the surface of the mixture and thus in direct contact with the mixture), while agitating said mixture, has been found to be particularly advantageous in breaking up primary agglomerates. Moreover the break up occurs progressively reducing the particle size of the dispersed particulate drug towards its primary particle size reaching a plateau at or near the primary particle size. Also from our observations, it seems that once primary agglomerates have been broken within liquefied propellant they do not re-agglomerate within the liquefied propellant, even after the power to the submersed ultrasonic probe(s) is turned off.

Surprisingly it has been found the effect of the ultrasonic power seems to depend in part on the volume of suspension it is applied to (in addition other factors such as amount of drug suspended and particular drug suspended). In this regard it has been found particularly favorable to apply at least a total of 200 kilowatts times seconds per liter (kW's/liter), more favorably at least a total of 450 kW·s/liter, and most favorably at least a total of 750 kW·s/liter. The particular, suitable amount of applied ultrasonic power (applied kilowatts times seconds per liter) for a particular manufacture operation generally may be determined for example by testing for particle size over treatment conditions and observing under which conditions the particle size value reaches, or closely reaches a plateau.

The one or more powered, submersed ultrasonic probes may be powered continuously or non-continuously, for example pulsed.

The use of two or more of powered, submersed ultrasonic probes is favorable in that the use of a plurality of probes allows for efficiency in terms of time, i.e. the ability to apply more ultrasonic energy to the dispersion in the same or shorter period of time than that of a single submersed ultrasonic probe.

For the yet enhanced facilitation of the breakdown of agglomerates, submersed ultrasonic probe(s) are desirably elongate as such a form is especially favorable in providing for strong cavitation as a result of high axial energy.

The above summary of the present invention is not intended to describe each disclosed embodiment or every implementation of the present invention. The description that follows more particularly exemplifies illustrative embodiments. Also further embodiments are described in dependent claims. In several places throughout the application, guidance is provided through lists of examples, which examples can be used individually and in various combinations. In each instance, the recited list serves only as a representative group and should not be interpreted as an exclusive list.

BRIEF DESCRIPTION OF DRAWINGS

The invention will now be described with reference to the accompanying drawings in which:

FIG. 1 represents a schematic cross-sectional view of a pressurized metered dose inhaler known in the art.

FIG. 2 represents a schematic flow chart of an exemplary manufacturing line.

FIGS. 3 and 4 show Andersen analysis results for Examples 1 and 2 with respect to fluticasone propionate and salmeterol xinafoate content, respectively.

FIGS. 5 to 9 show the particle size distribution for Examples 3 to 7, respectively.

FIG. 10 shows a bar chart of the particle size distribution data for Examples 3 to 7.

FIG. 11 shows a bar chart of the differences in particle size distribution data for Examples 3 to 7.

FIGS. 12 *a* and 12*b* represents photographs of sediments observed in Examples 8 to 10 and 11 to 13, respectively.

FIGS. 13 *a-c* to 14 *a-c* show the measured particle size distributions from Examples 8 to 10 and 11 to 13, respectively FIGS. 15 *a* and *b* represents SEM photographs of micronized fluticasone propionate starting materials FIGS. 16 *a* and *b* represents SEM photographs of fluticasone propionate particles observed after submersed-ultrasonic-probe-processing.

DETAILED DESCRIPTION

It is to be understood that the present invention covers all combinations of particular, suitable, desirable, favorable, advantageous and preferred aspects of the invention described herein.

For better understanding of the present invention, in the following an exemplary, well known pressurized metered dose inhaler (FIG. 1) will be first described. In particular, FIG. 1 shows a metered dose canister (10) including an aerosol container (1) fitted with a metered dose valve (11) (shown in its resting position) as part of a metered dose dispenser (100), in particular an inhaler.

Aerosol containers for medicinal inhalation canisters, such as metered dose canisters, are typically made of aluminum or an aluminum alloy. Aerosol containers may be made of other materials, such as stainless steel, glass, plastic or ceramics. Aerosol containers may be coated on part or all of their interior walls.

Returning to FIG. 1, the valve (11) is typically affixed onto the container via a cap or ferrule (typically made of aluminum or an aluminum alloy) which is generally provided as part of the valve assembly. The illustrated valve is a commercial valve marketed under the trade designation SPRAYMISER by 3M Company, St. Paul, Minn., USA. As shown in FIG. 1, the canister (10) is typically inserted into an actuator (5) including an appropriate patient port (6), such as a mouthpiece. For administration to the nasal cavities the patient port is generally provided in an appropriate form (e.g. smaller diameter tube, often sloping upwardly) for delivery through the nose. Actuators are generally made of a plastic, for example polypropylene or polyethylene. As can be seen from FIG. 1, the inner walls (2) of the container and the outer walls of the portion(s) of the metered dose valve located within the container defined a formulation chamber (3) in which aerosol formulation (4) is contained.

Medicinal aerosol formulations may include any drug or combination of drugs that may be delivered by an aerosol (e.g. administered by inhalation) and are typically provided in the form of drug particulates dispersed suspension in liquefied propellant, in particular liquefied HFA 134a and/or HFA 227. If desired or deemed necessary medicinal aerosol formulations may comprise other non-HFA 134a/HFA 227-propellant component or components, such as excipients, surfactants and suspending aids.

For manufacture of filled medicinal aerosol canisters, dry powder, particulate drug may be and is often supplied in micronized form from the producer of the active ingredient. Micronization can accomplished e.g. by using a fluid energy mill driven by compressed air, such as shown in 'Drug Delivery to the Respiratory Tract' ed. D. Ganderton and T. Jones, publ. Ellis Horwood, Chichester (1987) pages 89-90, or by repeated stepwise millings or by use of a closed loop milling system.

The primary particle size of drug (e.g. the size upon completion of micronization) generally has a mass median particle diameter of 5 microns or less, and most suitably said mass median diameter is in the range 0.8 to 3 microns, with at least 90% by mass of the particles having diameters below 5 microns, which can be determined, for example, by using an Andersen Cascade Impactor.

Depending on the particular valve and/or filling system used, aerosol formulation may be filled into the container either by cold-filling (in which chilled formulation is filled into the container and subsequently the valve is fitted onto the container) or by pressure filling (in which the valve is fitted onto the container and then formulation is pressure filled through the valve into the container).

As mentioned above, the present invention provides a method of manufacturing medicinal aerosol canisters containing a medicinal aerosol formulation comprising particulate drug dispersed in liquefied HFA 134a and/or HFA 227 propellant for use in a pressurized medicinal inhalation device, wherein the targeted number of canisters to be filled is greater than 500. As mentioned above, the described method is particularly suitable for large scale filling operations. The targeted number of canisters to be filled may be 2000 or more, in particular 5000 or more.

The method comprises the steps:

(a) providing a mixture comprising a particulate drug and liquefied HFA 134a and/or HFA 227 propellant and, optionally, other non-HFA 134a/HFA 227-propellant component or components;

either simultaneously or subsequently to said step of providing (step a), (b) subjecting said mixture to one or more powered ultrasonic probes, said one or more probes being submersed in said mixture, while agitating said mixture;

subsequently to said steps of providing and subjecting (steps a and b), (c) filling treated mixture into aerosol containers followed by attaching a valve to each filled container (cold filling) or alternatively filling treated mixture into aerosol containers through a valve pre-attached onto each container (pressure filling).

As mentioned above during step b, the step of subjecting, the mixture may be desirably subjected to at least a total of 200 applied kW's/liter. The mixture may be more desirably subjected to at least a total of 450 applied kW's/liter, most desirably at least a total of 750 applied kW's/liter. It will be appreciated that the ultrasonic probes are denoted with a particular power output rating given in Watts, and such power outputs can range from 50 W up to 16 kW or higher. Here it will be understood that a 1000 W rated ultrasonic probe submersed and running at 100% amplitude will have a 1000 W power output, or if running at 50% amplitude will have a 500 W power output. For example, subjecting a HFA 134a-based, 12.5 liter mixture at −60° C. (~18.4 kg with a density of ~1.475 ml) to ultrasonic energy from eight submersed ultrasonic probes each with a 4000 W rating for 900 seconds at 50% amplitude would mean that the total applied power output over time per liter would be 1152 kW's/liter. It is to be recognized that the efficiency of energy transfer to the fluid mixture would normally not be 100%. For example in the previous example, an efficiency of energy transfer of 90% would mean that the total energy transfer would be approximately 1037 kJ/liter. The particular efficiency of energy transfer depends on a number of factors including for example the ultrasonic probe itself (size and design) and process conditions (mixture temperature, viscosity, configuration of processing, and positioning of probe).

Ultrasonic probes may be any suitable ultrasonic transducer. They may be partially or fully submersed. They may extend into the mixture or be part of an interior containing-wall (e.g. plate mounted onto the interior wall of a vessel). They may have any suitable form. However, as mentioned above, submersed, elongate ultrasonic probe(s) are desirable, since the elongate form advantageously provides for strong cavitation as a result of high axial energy allowing for yet enhanced facilitation of the breakdown of agglomerates. Such probes are also advantageous in that the main portion of the energy (generally 90% plus) is typically coming from the tip allowing for ease in positioning (e.g. in a flowcell or in a mixing vessel) for submersion.

The ultrasonic power of the submersed probes may be provided as a continuously or non-continuously, for example pulsed. Pulsed powering may be advantageous in that the power is provided in bursts, and bursts of ultrasonic power seem to transmit more efficiently into the fluid mixture than continuous signals as the potential for phase cancellation from scattered signals is reduced. Where bursts are used, the pulses may typically be of half a second duration separated by periods of half a second with no signal.

As desired and/or needed, refrigeration may be used to ensure that the suspension does not overheat and/or that the temperature of the suspension is held at a constant value.

The steps of providing and subjecting (steps a and b) may comprise the operations of (i) adding particulate drug, liquefied HFA 134a and/or HFA 227 propellant and, if used, other non-HFA 134a/HFA 227-propellant component or components into a vessel, wherein said one or more powered, submersed ultrasonic probes are located in said vessel. Alternatively the steps of providing and subjecting (steps and b) may comprise the operations of (i) adding particulate drug, liquefied HFA 134a and/or HFA 227 propellant and, if used, other non-HFA 134a/HFA 227-propellant component or components into a vessel; (ii) circulating the mixture out of the vessel and back into the vessel through a re-circulation loop; and wherein said one or more powered, submersed ultrasonic probes are located in the re-circulation loop or in the vessel or, if applicable both. Agitation may be generated in the vessel by mixing, e.g. by high shear mixing. Movement through a re-circulation loop per se generates agitation. Regarding the option of having submersed probes in both the vessel and the re-circulation loop, it is understood that in this option two or more powered ultrasonic probes would be applied.

As indicated above, it can be appreciated that the use of two or more (i.e. a plurality) of powered, submersed ultrasonic probes may be advantageous in terms of time efficiency, greater power output in the same or shorter period of time relative to a single submersed ultrasonic probe.

The step of filling (step c) may comprise the operations of (i) transferring the treated mixture to a second vessel in a filling line; (ii) circulating the treated mixture out of the second vessel and back into the second vessel through a second re-circulation loop in the filling line; and (iii) delivering from the filling line via a filling head a metered aliquot of treated mixture into the aerosol container. Here, if desired to ensure the break up of any secondary agglomerates (agglomerates formed from any particles that have deposited out of the dispersion onto surfaces on the inside of the line), the step of filling may comprise subjecting said treated mixture to one or more powered ultrasonic probes, while agitating said treated mixture, said one or more probes being submersed in said treated mixture and located in the re-circulation loop of the filling line or in the vessel of the filling line or, if applicable, both. Again regarding the option of having submersed probes in both the second vessel and the second re-circulation loop, it is understood that in this option two or more powered ultrasonic probes would be applied.

In some methods, what could be termed a single batch method, in the step of providing (step a), the amounts of particulate drug, liquefied HFA 134a and/or HFA 227, and, if used, other component(s) may be equal to that amount deemed required for selected, targeted number of canisters to be filled.

In other methods, a concentrate may first be used. Here in the step of providing (step a) the amount of particulate drug is equal to that amount deemed required for selected, targeted number of canisters to be filled, and wherein the amount of liquefied HFA 134a and/or HFA 227 propellant is less than that amount deemed required for selected, targeted number of canisters to be filled and, if used, other component(s) are equal to or less than that amount deemed required for selected, targeted number of canisters to be filled. Here after the steps of providing and subjecting (steps and b), but prior to the step of filling (step c), the method comprises an additional step including combining additional liquefied HFA 134a and/or HFA 227 propellant and, if applicable, other component(s) with the treated mixture such that amount of propellant and other component(s), if used, are equal to those amount(s) deemed required for selected, targeted number of canisters to be filled.

The latter concentrate method may be better appreciated by looking at FIG. 2 showing a schematic flow chart of part of an exemplary process line suitable for carrying out methods described herein. The exemplary illustrated process line includes a first vessel (21), referred to in the following as the concentrate vessel, shown towards the middle of the illustrated flowchart. The concentrate vessel (21) is fitted with a recirculation loop including a pump (25), flow cell (24) fitted with one or more ultrasonic probes (23) that will be submersed in the fluid flowing through the flow cell and a heat exchanger (22). The first vessel and the recirculation loop may be considered the mixing line. The flow chart also shows a filling line, in fact, only part of a filling line as the only the filling head (37) is shown. The illustrated line includes a second vessel (36), referred to in the following as the batch vessel. The batch vessel is also fitted with a recirculation loop including the filling head (37) and two pumps (38, 41).

Referring to the flow chart, the following describes an exemplary process of manufacturing medicinal aerosol canisters: An amount of liquefied propellant (e.g. HFA 134a) equal to that amount deemed required for selected, targeted number of canisters and, for example, an amount of excipient (e.g. ethanol) equal to that amount deemed required for selected, targeted number of canisters to be filled are added to the batch vessel (36). The contents of batch vessel is mixed with a mixer (40) (e.g. with a paddle mixer or, if desired, a high shear mixer). A portion of the propellant/excipient mixture from the batch vessel (36) is added to the concentrate vessel (21) through a feed line (39) and an amount of particulate drug (e.g. a single drug or a drug combination) equal to that amount deemed required for selected, targeted number of canisters to be filled is added to concentrate vessel (21). The mixture of propellant, excipient and particulate drug in concentrate vessel (21) is mixed with a mixer (27) (e.g. a high shear mixer) and pumped through the re-circulation loop, subjecting the mixture to one or more powered, submersed ultrasonic probes (23) in the flow cell (24) and thereby breaking up primary agglomerates in the mixture as the mixture passes through the flow cell. After passing the flow cell the mixture passes a refrigeration unit (22) returning then to the concentrate vessel (21) and then pumped back to the re-circulation loop. The concentrate mixture is continuously passed through the re-circulation loop and treated with the submersed ultrasonic probe(s). The particular treatment conditions (e.g. applied kW·s/l) would normally be pre-determined for a particular manufacture filling operation by testing for particle size over treatment conditions (e.g. power output, time) and observing under which conditions the value for particle size reaches or closely approaches a plateau.

After suitable treatment with the submersed ultrasonic probe(s), the processed mixture in concentrate vessel (21) is transferred to the batch vessel (36) through a feed line (26). In this manner the propellant/excipient mixture in the batch vessel combines with the processed mixture and the amounts of particulate drug, propellant and excipient are equal to those amount(s) deemed required for selected, targeted number of canisters to be filled. To avoid sedimentation of the particulate drug, the mixture is mixed with an appropriate mixer (40) in the batch vessel (36). The combined mixture is pumped to a filling head (37) where the treated mixture is filled into aerosol containers (not illustrated) for example by filling containers and after filling each container is sealed by attaching a valve (e.g. metered dose valve) thereto.

Medicinal aerosol canisters, in particular metered dose canisters, produced using methods disclosed herein, may be advantageously utilized as part of dispensers for the administration of medicament through oral, transmucosal (e.g. buccal, sublingual), vaginal, rectal, ocular or aural delivery. Manufactured canisters disclosed herein, in particular canisters fitted with a metered dose valve, are particularly suited for delivering medicaments by inhalation to a patient. Accordingly, manufactured canisters disclosed herein and dispensers comprising manufactured canisters described herein are particularly suitable for use in or as pressurized metered dose inhalers, respectively.

For delivery by inhalation, suitable medicaments include any drug or drugs combination that may be administered by inhalation and that can be provided in the form of particles suitable for suspension in liquefied propellant, in particular liquefied HFA 134a and/or HFA 227.

Suitable drugs include those for the treatment of respiratory disorders, e.g., bronchodilators, anti-inflammatories (e.g. corticosteroids), anti-allergics, anti-asthmatics, anti-histamines, and anti-cholinergic agents. Other drugs such as anorectics, anti-depressants, anti-hypertensive agents, anti-neoplastic agents, anti-tussives, anti-anginals, anti-infectives (e.g. antibacterials, antibiotics, anti-virals), anti-migraine drugs, anti-peptics, dopaminergic agents, analgesics, beta-adrenergic blocking agents, cardiovascular drugs, hypoglaecemics, immunomodulators, lung surfactants, prostaglandins, sympathomimetics, tranquilizers, steroids, vitamins, sex hormones, vaccines, therapeutic sense or anti-sense nucleic acids, and other therapeutic proteins and therapeutic peptides may also be employed for delivery by inhalation.

Exemplary drugs which may be employed for delivery by inhalation include but are not limited to: albuterol, terbutaline, fenoterol, metaproterenol, isoproterenol, isoetharine, bitolterol, epinephrine, tulobuterol, bambuterol, reproterol, adrenaline, ipratropium, oxitropium, tiotropium, beclomethasone, betamethasone, flunisolide, budesonide, mometasone, ciclesonide, rofleponide, aminophylline, dyphylline, theophylline, cromolyn sodium, nedocromil sodium, ketotifen, azelastine, ergotamine, cyclosporine, salmeterol, fluticasone, formoterol, procaterol, indacaterol, TA2005, omalizumab, montelukast, zafirlukast, betamethasone sodium phosphate, dexamethasone, dexamethasone sodium phosphate, dexamethasone acetate, prednisone, methylprednisolone acetate, zileuton, insulin, atropine, prednisolone, benzphetamine, chlorphentermine, amitriptyline, imipramine, clonidine, actinomycin c, bromocriptine, buprenorphine, pentamidine, calcitonin, leuprolide, alpha-1-antitrypsin, interferons, propranolol, lacicortone, triamcinolone, dinoprost, xylometazoline, diazepam, lorazepam, folic acid, nicotinamide, clenbuterol, ethinyloestradiol, levonorgestrel, and pharmaceutically acceptable salts and esters thereof such as albuterol sulfate, formoterol fumarate, salmeterol xinafoate, beclomethasone dipropionate, triamcinolone acetonide, fluticasone propionate, tiotropium bromide, leuprolide acetate and mometasone furoate.

Further drugs that may also be delivered by inhalation include but are not limited to aspirin, acetaminophen, ibuprofen, naproxen sodium, buprenorphine hydrochloride, propoxyphene hydrochloride, propoxyphene napsylate, meperidine hydrochloride, hydromorphone hydrochloride, morphine sulfate, fentanyl citrate, oxycodone hydrochloride, codeine phosphate, dihydrocodeine bitartrate, pentazocine hydrochloride, hydrocodone bitartrate, levorphanol tartrate, diflunisal, diamorphine, trolamine salicylate, methadone hydrochloride, nalbuphine hydrochloride, nalorphine, tetrahydrocannabinol, mefenamic acid, butorphanol tartrate, choline salicylate, butalbital, phenyltoloxamine citrate, diphenhydramine citrate, methotrimeprazine, cinnamedrine hydrochloride, meprobamate, ergotamine tartrate, propanolol hydrochloride, isometheptene mucate, dichloralphenazone, sumatriptan, rizatriptan, zolmitriptan, naratriptan, eletriptan, barbiturates (e.g., pentobarbital, pentobarbital sodium, secobarbital sodium), benzodiazapines (e.g., flurazepam hydrochloride, triazolam, tomazeparm, midazolam hydrochloride, lorazepam, buspirone hydrochloride, prazepam, chlordiazepoxide hydrochloride, oxazepam, clorazepate dipotassium, diazepam, temazepam), lidocaine, prilocalne, xylocalne, beta-adrenergic blockers, calcium channel blockers (e.g., nifedipine, diltiazem hydrochloride, and the like), nitrates (e.g., nitroglycerin, isosorbide dinitrate, pentaerythritol tetranitrate, erythrityl tetranitrate), hydroxyzine pamoate, hydroxyzine hydrochloride, alprazolam, droperidol, halazepam, chlormezanone, haloperidol, loxapine succinate, loxapine hydrochloride, thioridazine, thioridazine hydrochloride, thiothixene, fluphenazine hydrochloride, fluphenazine decanoate, fluphenazine enanthate, trifluoperazine hydrochloride, chlorpromazine hydrochloride, perphenazine, lithium citrate, prochlorperazine, lithium carbonate, bretylium tosylate, esmolol hydrochloride, verapamil hydrochloride, amiodarone, encamide hydrochloride, digoxin, digitoxin, mexiletine hydrochloride, disopyramide phosphate, procainamide hydrochloride, quinidine sulfate, quinidine gluconate, quinidine polygalacturonate, flecamide acetate, tocamide hydrochloride, lidocaine hydrochloride, phenylbutazone, sulindac, penicillamine, salsalate, piroxicam, azathioprine, indomethacin, meclofenamate sodium, gold sodium thiomalate, ketoprofen, auranofin, aurothioglucose, tolmetin sodium, colchicine, allopurinol, heparin, heparin sodium, warfarin sodium, urokinase, streptokinase, altoplase, aminocaproic acid, pentoxifylline, empirin, ascriptin, valproic acid, divalproate sodium, phenyloin, phenyloin sodium, clonazepam, primidone, phenobarbitol, phenobarbitol sodium, carbamazepine, amobarbital sodium, methsuximide, metharbital, mephobarbital, mephenyloin, phensuximide, paramethadione, ethotoin, phenacemide, secobarbitol sodium, clorazepate dipotassium, trimethadione, ethosuximide, doxepin hydrochloride, amoxapine, trazodone hydrochloride, amitriptyline hydrochloride, maprotiline hydrochloride, phenelzine sulfate, desipramine hydrochloride, nortriptyline hydrochloride, tranylcypromine sulfate, fluoxetine hydrochloride, doxepin hydrochloride, imipramine hydrochloride, imipramine pamoate, nortriptyline, amitriptyline hydrochloride, isocarboxazid, desipramine hydrochloride, trimipramine maleate, protriptyline hydrochloride, hydroxyzine hydrochloride, diphenhydramine hydrochloride, chlorpheniramine maleate, brompheniramine maleate, clemastine, azelastine, cyproheptadine hydrochloride, terfenadine citrate, clemastine, triprolidine hydrochloride, carbinoxamine maleate, diphenylpyraline hydrochloride, phenindamine tartrate, lamivudine, abacavir, acyclovir, gancyclovir, valganciclovir, cidofovir, foscarnet, azatadine maleate, tripelennamine hydrochloride, dexchlorpheniramine maleate, methdilazine hydrochloride, trimprazine tartrate, trimethaphan camsylate, phenoxybenzamine hydrochloride, pargyline hydrochloride, deserpidine, diazoxide, guanethidine monosulfate, minoxidil, rescinnamine, sodium nitroprusside, rauwolfia serpentina, alseroxylon, phentolamine mesylate, reserpine, calcitonin, parathyroid hormone, acitretin, amikacin sulfate, aztreonam, benzydamine, calcipotriol, chloramphenicol, chloramphenicol palmitate, chloramphenicol sodium succinate, ciprofloxacin hydrochloride, clindamycin hydrochloride, clindamycin palmitate, clindamycin phosphate, efalizumab, metronidazole, metronidazole hydrochloride, gentamicin sulfate, lincomycin hydrochloride, tobramycin sulfate, tacrolimus, vancomycin hydrochloride, polymyxin B sulfate, colistimethate sodium, colistin sulfate, tetracycline, griseofulvin, keloconazole, interferon gamma, zidovudine, amantadine hydrochloride, ribavirin, acyclovir, pentamidine e.g. pentamidine isoethionate, cephalosporins (e.g., cefazolin sodium, cephradine, cefaclor, cephapirin sodium, ceftizoxime sodium, cefoperazone sodium, cefotetan disodium, cefutoxime axotil, cefotaxime sodium, cefadroxil monohydrate, ceftazidime, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, cefuroxime sodium, and the like), penicillins (e.g., ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G potassium, penicillin G procaine, methicillin sodium, nafcillin sodium, and the like), erythromycins (e.g., erythromycin ethylsuccinate, erythromycin, erythromycin estolate, erythromycin lactobionate, erythromycin siearate, erythromycin ethylsuccinate, and the like), tetracyclines (e.g., tetracycline hydrochloride, doxycycline hyclate, minocycline hydrochloride, GM-CSF, ephedrine, pseudoephedrine, ammonium chloride, androgens (e.g., danazol, testosterone cypionate, fluoxymesterone, ethyltostosterone, testosterone enanihate, methyltestosterone, fluoxymesterone, testosterone cypionate), estrogens (e.g., estradiol, estropipate, conjugated estrogens), progestins (e.g., methoxyprogesterone acetate, norethindrone acetate), levothyroxine sodium, human insulin, purified beef insulin, purified pork insulin, glyburide, chlorpropamide, glipizide, tolbutamide, tolazamide, rosiglitazone, pioglitazone, troglitazone, clofibrate, dextrothyroxine sodium, probucol, lovastatin, rosuvastatin, niacin, DNase, alginase, superoxide dismutase, lipase, calcitonion, alpha-1-antitrypsin, interferons, sense or anti-sense nucleic acids encoding any protein suitable for delivery by inhalation, erythropoietin, famotidine, cimetidine, ranitidine hydrochloride, omeprazole, esomeprazole, lanzoprazole, meclizine hydrochloride, nabilone, prochlorperazine, dimenhydrinate, promethazine hydrochloride, thiethylperazine, scopolamine, sildenafil, vardenafil, cilomilast, imiquimod or resiquimod. Where appropriate, these drugs may be delivered in alternative salts forms.

Excipients may include for example, surfactants, co-solvent suspending aids, and/or particulate bulking agents.

Suitable surfactants include those disclosed in EP 372777, GB 837465 and GB 994734, each incorporated herein by reference. Span 85, oleic acid and/or lecithin are commonly used in medicinal aerosol formulations. Other suitable surfactants for use in medicinal aerosol formulations include HFA-soluble fluorocarbons such as those referred to in WO 91/11173, GB 2263064, each incorporated herein by reference, as well as polyethyleneoxide, polyoxyethylene-oxypropylene block copolymers such as members of the Synperonic PE series (Croda International plc), polyoxypropylenes, polyoxyethylene-polyoxypropylene-ethylenediamine copolymers such as members of the Synperonic T series, castor oil ethoxylates such as Alakasurf CO-40, acetylated monoglycerides (e.g. Myvacet 9-40 or 9-45 from Farma International), polyvinyl pyrrolidone, polyvinylacetate, polyvinyl alcohol, polymers of acrylic acid, methacrylic acid and copolymers thereof, polyoxyethylene glyceryl trioleate (TagatTO), Polyoxyethylene glyceryl monooleate (TagatO or TagatO2 from Degussa), Diol-diacids such as those disclosed in WO 94/21228, incorporated herein by reference, oligolactic acid and derivatives thereof, such as those disclosed in WO 94/21229, incorporated herein by reference, functionalized PEGs such as those disclosed in WO 2003/059317, incorporated herein by reference, amide-ester excipients such as those disclosed in WO 2003/059331, incorporated herein by reference, Propoxylated PEG (Antarox 31R1 from Solvay), polyoxyethylene glycerol esters such as those disclosed in U.S. Pat. No. 5,536,444, incorporated herein by reference, protective colloids such as those described in WO 95/15151, incorporated herein by reference, glyceryl triesters, capr(yl) ic diglyceryl succinates (e.g. Miglyol 829 from Condea Chemie GmbH), Vitamin E acetate, tocopherol (Vitamin E), polyglycolized polyglyceride (e.g. Labrafac Hydro WL 1219 from Gattefosse, Gennevilliers, France), polypropylene glycol, polyethylene glycol e.g. PEG300, aminoacids or derivatives such as disclosed in U.S. Pat. No. 6,136,294 incorporated herein by reference, and other surfactants in the same chemical family as the above but differing in chain length of alkyl or polyalkoxy groups.

Suitable co-solvents may include ethanol, propanol, isopropanol, and other alcohols, glycerol, polyethylene glycol 400, propylene glycol, decanol, sorbitol, mannitol, lactitol, maltitol, glycofurol, dipropylene glycol, propylene glycol diesters of medium chain fatty acids (e.g. Miglyol 840), triglyceride esters of medium chain fatty acids (e.g. Miglyol 810, 812), perfluorocyclobutane, perfluoropentane, perfluorodimethylcyclobutane, menthol, eucapyptus oil, propylene glycol monolaurate (Lauroglycol), diethylene glycol monoethyl ester (Transcutol), isopropyl myristate, saturated hydrocarbons in liquid form and essential oils. Ethanol is commonly used in medicinal aerosol formulations.

Suitable suspending aids may include lactose, glucose, sucrose, D(+)trehalose, as well as their various hydrates, anomers and/or enantiomers, other saccharides such as D-galactose, maltose, D(+)raffinose pentahydrate, sodium saccharin, polysaccharides such as starches, modified celluloses, dextrins, dextrans, DL-alanine, other aminoacids or derivatives such as disclosed in U.S. Pat. No. 6,136,294 incorporated herein by reference, ascorbic acid, sodium sulphate, cetyl pyridinium chloride or bromide other salts e.g. sodium chloride, calcium carbonate, sodium tartrate, calcium lactate, or other organic compounds e.g. urea or propyliodone.

EXPERIMENTAL SECTION

Examples 1 and 2

Example 1

Ethanol (12.02 g) was weighed into a 1 liter stainless steel vessel and the vessel was cooled to −70° C. Liquefied HFA-134a (about 600 g) was transferred to the vessel. The temperature was adjusted to −55° C., during which the vessel was lightly sealed with PARAFILM™ sealing film to protect against ingress of moisture. Ultrasonic apparatus consisting of a Hielscher UIP1000 ultrasonic processor with a 40 mm diameter sonotrode probe was maneuvered over the vessel and the probe tip was submersed to a depth of approximately 4 cm into the chilled propellant mix. The probe and vessel were shrouded with polythene film to replace the PARAFILM™ sealing film. With the ultrasonic power unit with a 1000 W rating switched on to half power (50% amplitude; 500 W) for about 30-45 seconds the micronized fluticasone propionate (2.156 g; from producer lot known to contain agglomerates) and micronized salmeterol xinafoate (0.629 g) were added to the vessel by momentarily raising the shroud. The ultrasonic apparatus was then turned up to full power 1000 W (100% amplitude) and operated for 5 minutes with occasional swirling of the vessel to ensure effective bulk flow of particles in the propellant mix. The mixture thus prepared was weighed then added to a 2 litre batching vessel of a cold filling apparatus with refrigeration. Liquefied HFA134a was added such that the resulting total weight of HFA134a allowing for evaporation during the aforementioned processing was 1187 g. The resulting formulation was filled in 12 g aliquots into 10 ml aluminium cans having a fluoropolymer internal coating which were then sealed with 63 µl metering valves.

Reference Example 2

The procedure of Example 1 was repeated with the exception that instead of using a submersed, elongate ultrasonic probe, a Silverson Model L4R high shear mixer running at 7000 RPM was applied.

Figure 3:
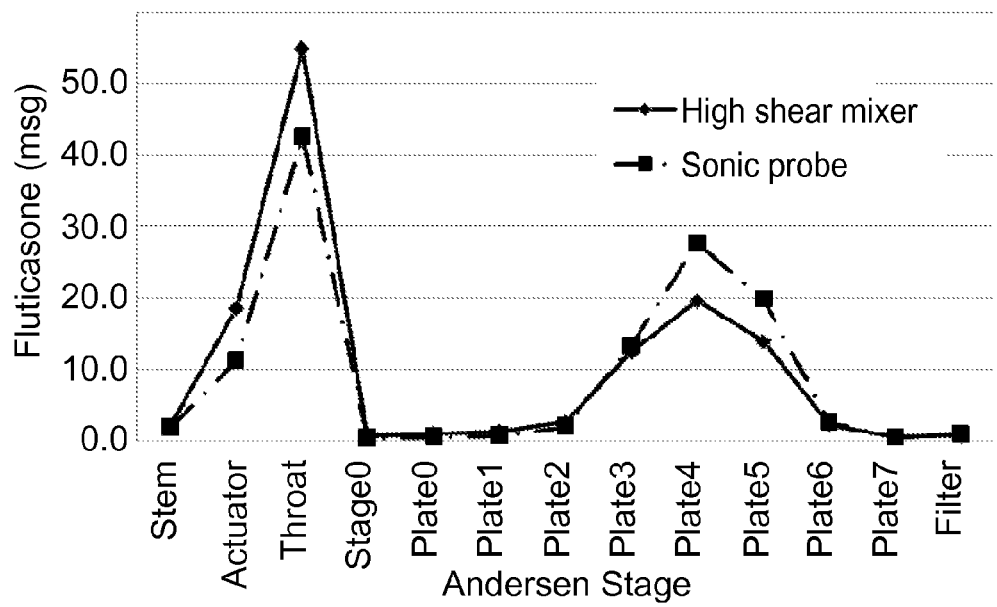
Figure 4:
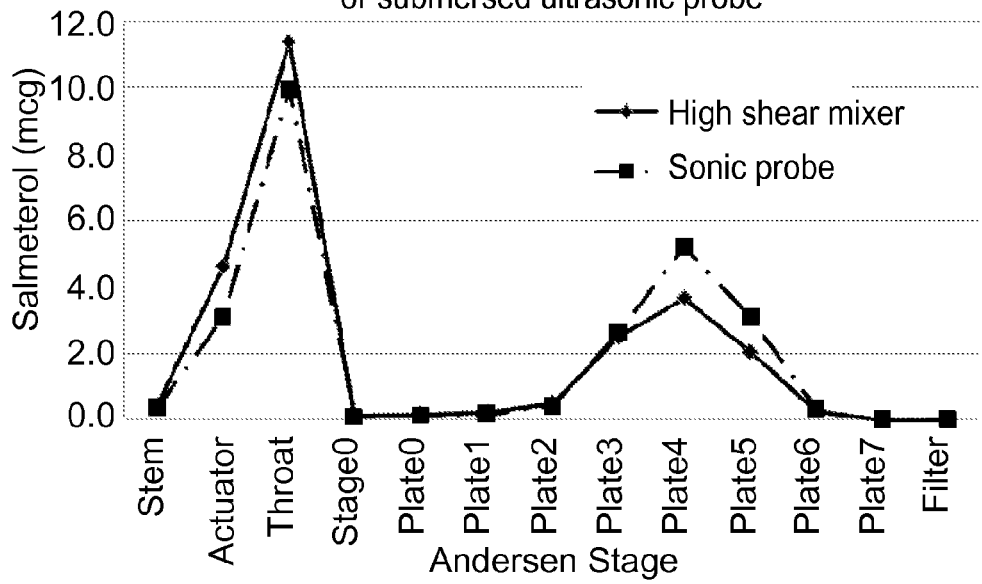
Figure 5:
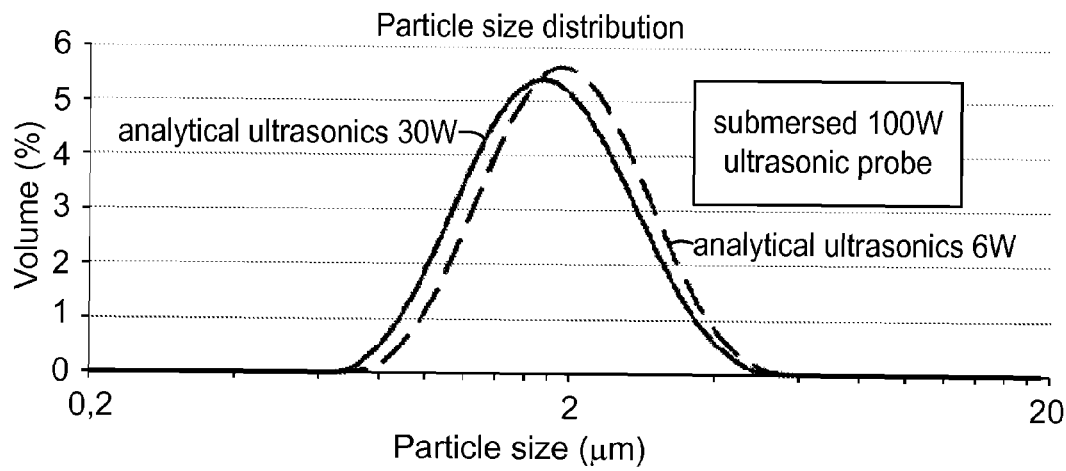
Figure 6:
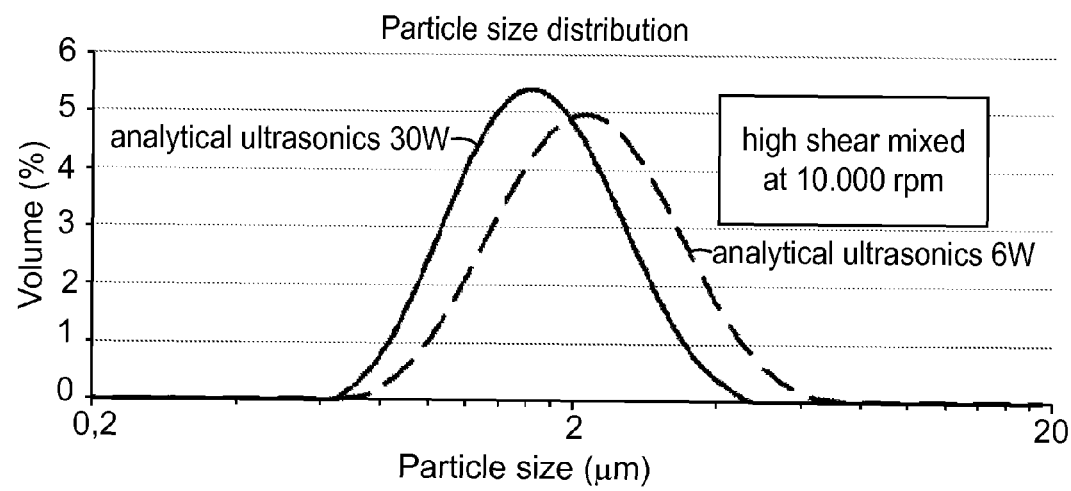
Figure 7:
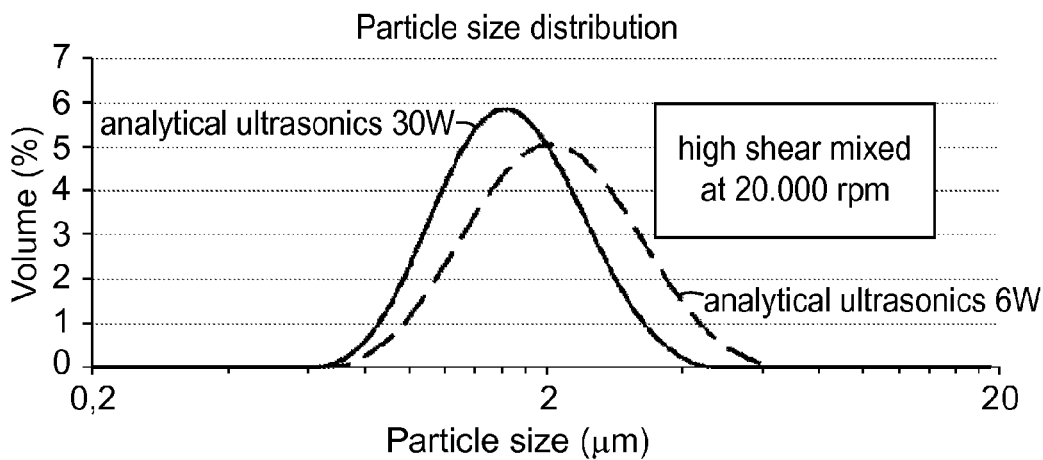
Figure 8:
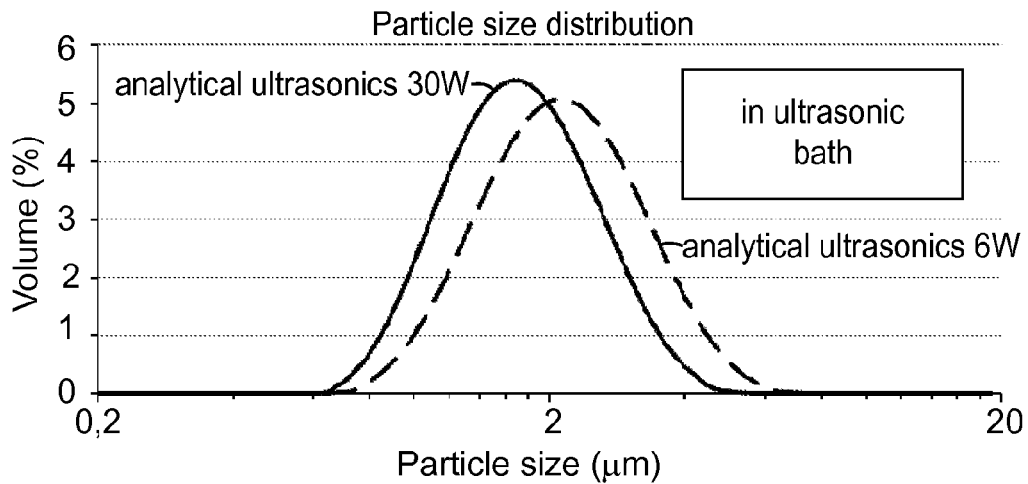
Figure 9:
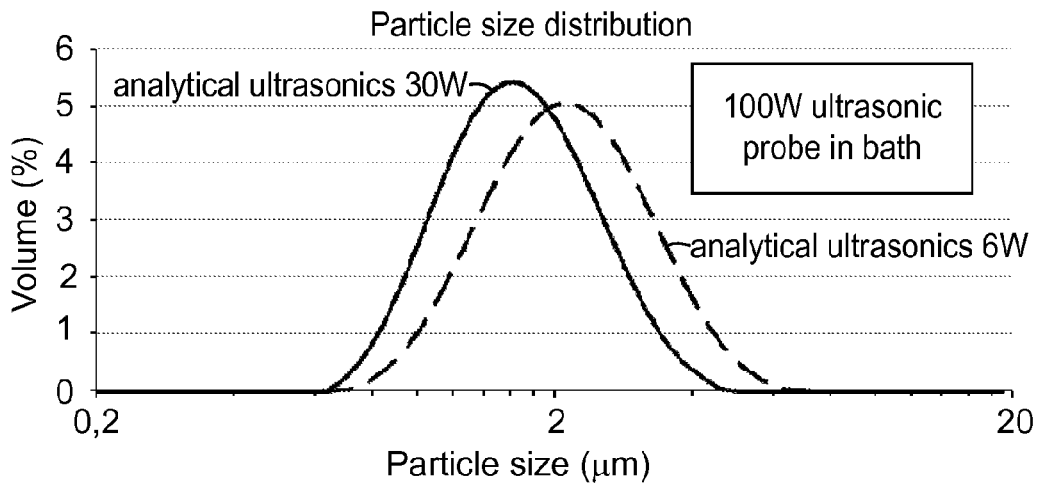

Andersen Analyses: The aerodynamic particle size distribution emitted from 10 inhaler units from Example 1 and Reference Example 2 were evaluated using the Andersen Mark II Cascade Impactor (ACI) (Thermo Fisher Scientific, Waltham, Mass.). Three Andersen cascade impactor (ACI) tests were conducted on each of the formulations by coupling the MDI to a USP inlet ('Throat') and actuating six times into the ACI setup. The flow rate during testing was 28.3 liters per minute (1 pm). The drug collected on the valve stem, actuator, Throat, jet for Stage 0 of the ACI, all of the ACI impaction plates (plates 0-7), and the filter was determined by rinsing each individual section with a known volume of solvent 85% Methanol: 15% Ammonium Acetate Solution): The recovered samples were analyzed using an HPLC assay. The impaction plates of the ACI were not coated for any of the tests. The averaged results from each population are shown in FIG. 3 with respect to fluticasone propionate content and FIG. 4 with respect to salmeterol xinafoate content.

Examples 3 to 7

Micronized fluticasone propionate (70 mg) was weighed into each of 5 glass sample vials. Model dispersant (1% ethanol in a mixture of isooctane and decafluoropentane in a ratio by weight of 52:48) (25 ml) was then added to each vial. Each vial was then subjected to a specific dispersion regime detailed below using either a high shear mixer (model IKA T25 Ultra Turrax); a sonic probe (model Hielscher UIP 100H with 7 mm sonotrode; 100 W rating) or an ultrasonic bath, (model Sonorex RK106S) containing 1 litre of water. The processing duration for each dispersion regime was 2 minutes.

| Sample | Dispersion regime | Specific conditions |
| --- | --- | --- |
| Ex. 3 | Elongate ultrasonic probe submersed in dispersion (referred to in the following as "submersed ultrasonic probe") | 100 W, Amplitude setting 100% with 0.5 seconds pulse width |
| Ref. Ex. 4 | High shear mixing - medium intensity | 10,000 RPM |
| Ref. Ex. 5 | High shear mixing - high intensity | 20,000 RPM |
| Ref. Ex. 6 | Sample vial immersed in ultrasonic bath | bath activated |
| Ref. Ex. 7 | Sample vial immersed in ultrasonic bath with probe adjacent to the vial (2 cm distance) in the water | Bath not activated but ultrasonic probe activated with amplitude setting 100 with 0.5 seconds pulse width |

1. Dispersion Sedimentation

Each dispersion was added to a separate stoppered 25 ml measuring cylinder and shaken for 5 seconds and then left to stand. After 2 minutes standing the sediment height was read from the graduations on the measuring cylinders.

2. Particle Size Analysis by Laser Diffraction

Particle Sizing Procedure

Suspension of sample to be measured was added dropwise to the 100 ml dispersant (0.05 volume % lecithin in iso-octane) in the presentation unit of the Malvern Mastersizer 2000 SN 34355-36 ARD 0326 while circulating with the stirrer on 3000 rpm to obtain an obscuration measurement of between 10 and 12. After 2 minutes recirculation an ultrasonic probe Sonics Vibracell from Sonics and Materials Inc, USA, Model was placed in the dispersant was powered up. To assure dispersion of any flocculates in the sample, the ultrasonic probe was powered to 6 W for a period of 4 minutes. After switching the ultrasonic power off to and allowing a dwell time of 2 minutes, measurements (ten readings) were made on the sample. To break up any primary agglomerates remaining after manufacture of the sample, the probe was reinserted into the dispersant and powered to 30 W for a period of 4 minutes. Once again the probe was removed and then after a dwell time of 2 minutes, measurements (ten readings) were made on the sample. Tests were performed on all samples in duplicate. The Mie theory optical properties for fluticasone propionate were set to refractive index=1.750, absorbance=0.050.

Results

Figure 11:
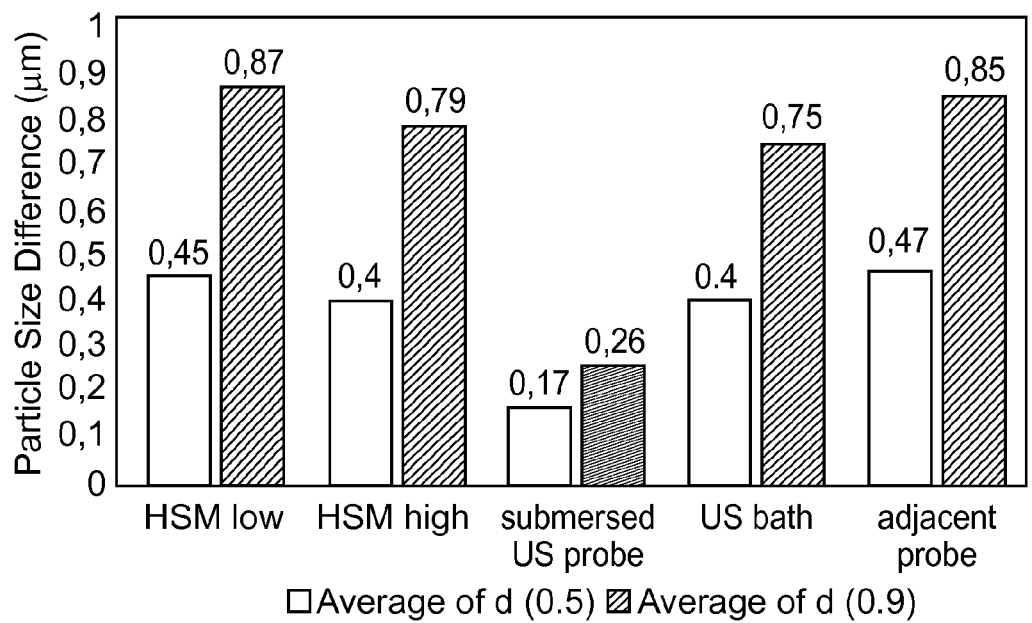

FIGS. 5 to 9 show the particle size distribution of Samples 3 to 7, respectively. It will be appreciated that for the samples produced using the submersed ultrasonic probe, the 6 W and 30 W measurements essentially overlap demonstrating that the method is successful in removing nearly all primary agglomerates. The distributions for the other samples show a significantly higher particle size in the 6 W measurements pointing to a significant amount of primary agglomerates in the dispersions. FIG. 10 shows a bar chart of the particle size distribution data of the 6 W measurements. Here is a distinct difference between the sample prepared using a submersed ultrasonic probe (d(0.5)=1.86 micron; d(0.9)=2.98 micron) compared to the other samples (average of four reference samples: d(0.5)=2.15 micron; d(0.9)=3.62 microns) can be recognized. FIG. 11 shows a bar chart of the differences of the particle size distribution data for the 6 W and 30 W measurements. This chart shows that the difference in size measured for the sample prepared with the submersed ultrasonic probe is low and much lower than that observed for the other prepared samples.

Examples 8 to 13

The equipment and materials used for manufacture of samples are the same as listed under Examples 3 to 7, except that the micronized fluticasone propionate used was from a different producer lot (also known to contain agglomerates).

Method

Fluticasone propionate (70 mg) was weighed into each of 5 glass sample vials. Model dispersant (25 ml) was then added to each vial. Each vial was then subjected to a specific dispersion regime and processing duration detailed below.

| Sample | Dispersion regime, conditions | Duration |
| --- | --- | --- |
| Ex. 8 | Submersed, elongate ultrasonic probe, Amplitude setting 100%; 0.5 seconds pulse width | 2 minutes |
| Ex. 9 | Submersed ultrasonic probe as in Ex. 8, | 4 minutes |
| Ex. 10 | Submersed ultrasonic probe as in Ex. 8 | 8 minutes |
| Ref. Ex. 11 | High shear mixing, 20,000 RPM | 2 minutes |
| Ref. Ex. 12 | High shear mixing, 20,000 RPM | 4 minutes |
| Ref. Ex. 13 | High shear mixing, 20,000 RPM | 8 minutes |

1. Dispersion Sedimentation

Figure 12A:
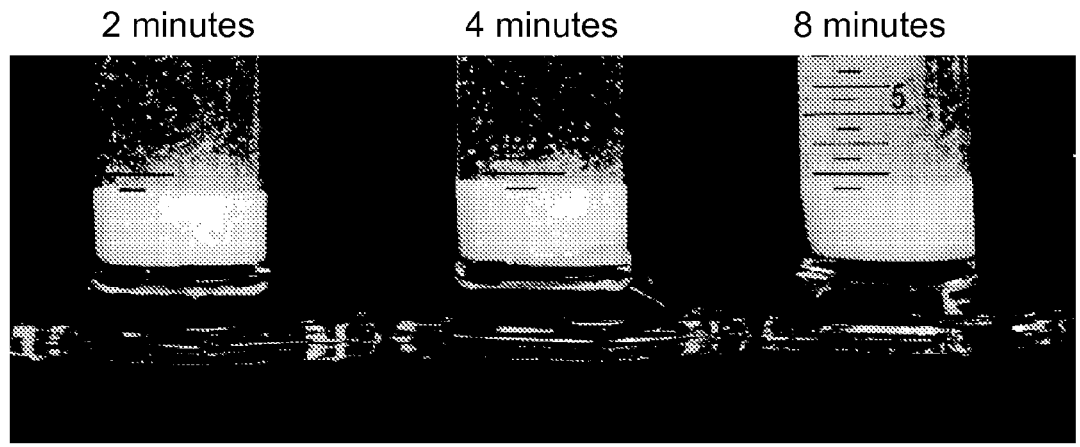
Figure 12B:
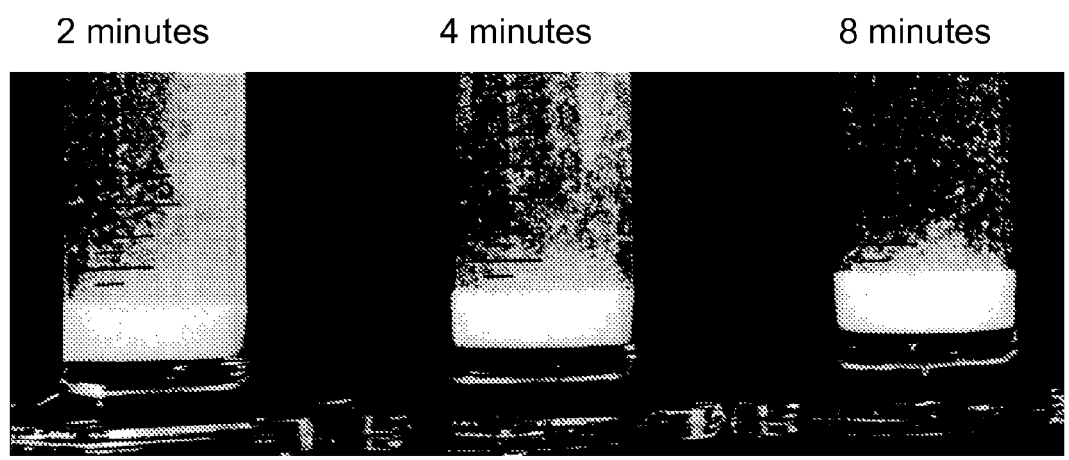

Each prepared, dispersed formulation was added to a separate 25 ml measuring cylinder. After closing each cylinder with a stopper, they were shaken for 5 seconds, left to stand for two minutes, and then photographs of the sediment were taken. These are provided in FIG. 12.

2. Particle Size Analysis by Laser Diffraction

Figure 13A:
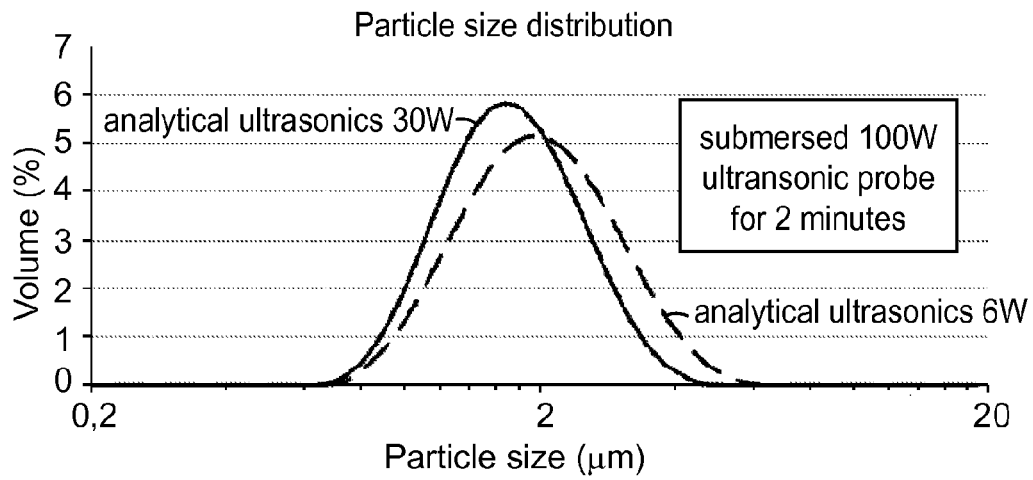
Figure 13B:
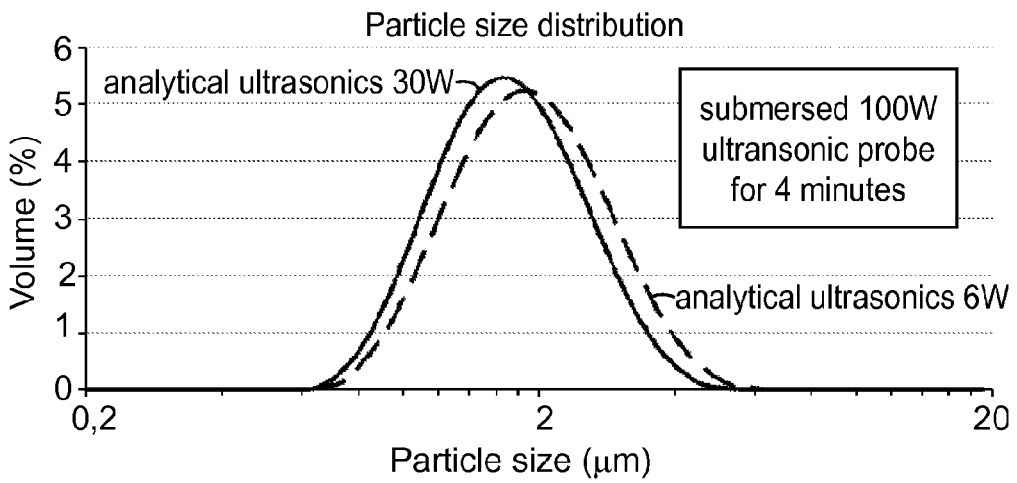
Figure 13C:
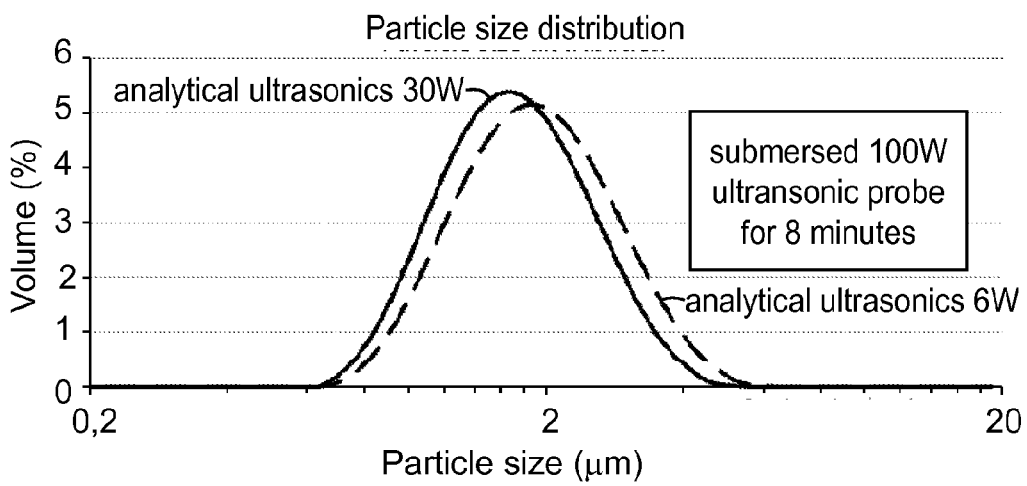
Figure 14A:
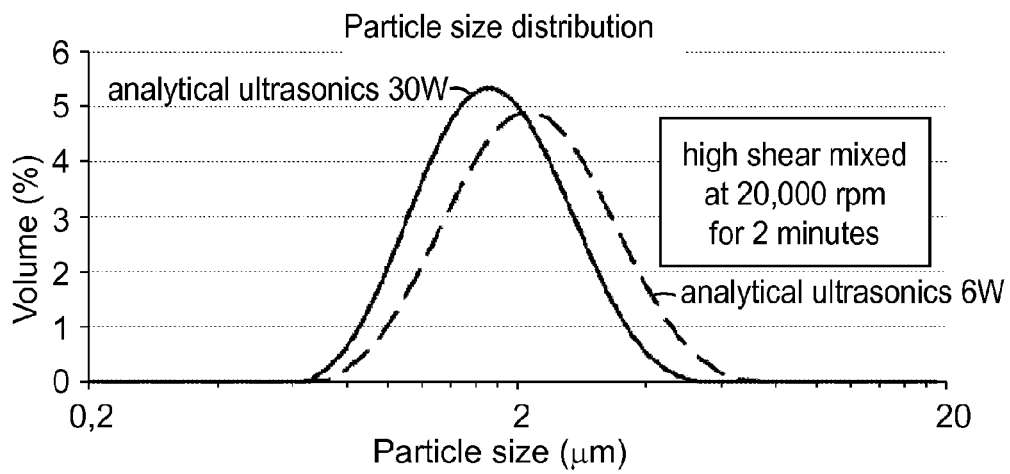
Figure 14B:
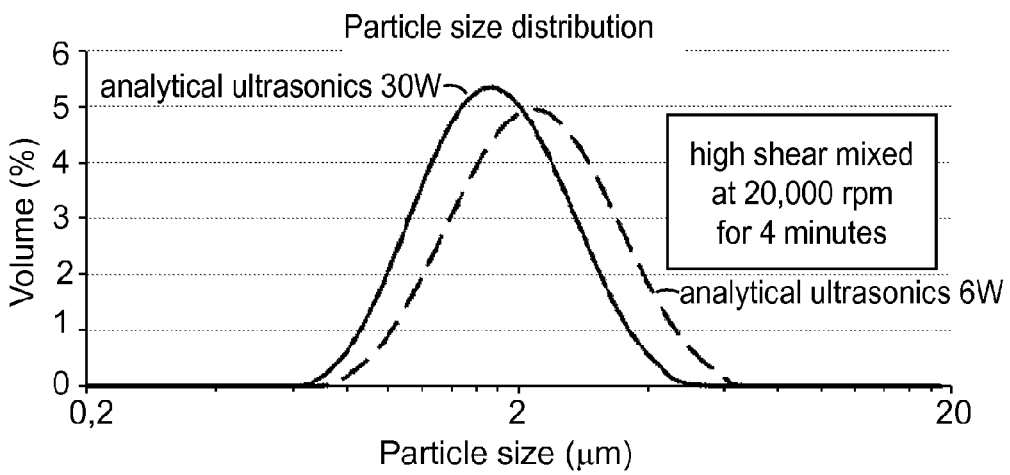
Figure 14C:
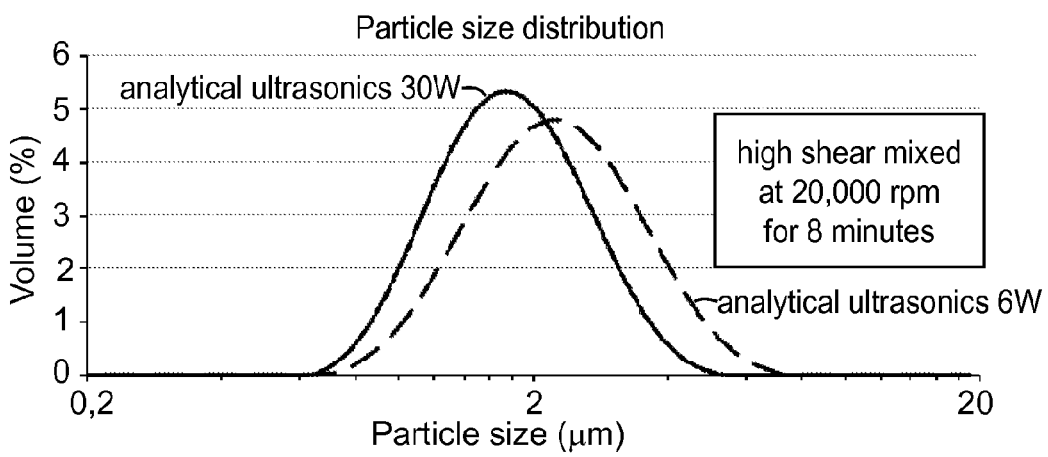

Equipment, materials and measurement procedure used for particle size analysis are essentially same as that described for Examples 3 to 7. FIGS. 13 a-c to 14 a-c show the measured particle size distributions of Samples 8 to 10 and 11 to 13, respectively. It will be appreciated that for the samples produced using the submersed ultrasonic probe, the 6 W and 30 W measurements essentially overlap demonstrating that the method is successful in removing nearly all primary agglomerates. The distributions for the high shear mixed samples show a significantly higher particle size in the 6 W measurements and a significant gap between 6 W and 30 W measurement curves pointing to a significantly amount of primary agglomerates in the dispersions after high shear mixing. Also the distributions for the high shear mixed samples at a processing durations of 2, 4 and 8 minutes showed no significant difference suggesting the a longer processing duration does not effect any significantly higher removal of agglomerates.

Exemplary SEM Photographs

FIGS. 15a and b show SEM photographs of the typical type of agglomerates observed micronized fluticasone propionate starting materials. FIGS. 16 a and b represents SEM photographs of typical fluticasone propionate particle dispersions observed after processing with a submersed, elongate ultrasonic-probe.

The invention claimed is:

1. A method of manufacturing medicinal aerosol canisters containing a medicinal formulation comprising particulate drug dispersed in liquefied HFA 134a and/or HFA 227 propellant, wherein the targeted number of canisters to be filled is greater than 500, the method comprising the steps:
   (a) providing a mixture comprising a particulate drug and liquefied HFA 134a and/or HFA 227 propellant and, optionally, other non-HFA 134a/HFA 227-propellant component or components;
   either simultaneously or subsequently to said providing (step a),
   (b) subjecting said mixture to one or more powered ultrasonic probes, said one or more probes being submersed in said mixture, while agitating said mixture;
   subsequently to said steps of providing and subjecting (steps a and b),
   (c) filling treated mixture into aerosol containers followed by attaching a valve to each filled container (cold filling) resulting in a filled canister or alternatively filling treated mixture into aerosol containers through a valve pre-attached onto each container (pressure filling) resulting in a filled canister, where said mixture is subjected to at least a total of 200 applied kilowatts times seconds per liter (kW·s/liter).

2. A method according to claim 1, wherein said one or more powered, submersed ultrasonic probes are powered continuously.

3. A method according to claim 1, wherein the steps of providing and subjecting (steps a and b) comprise the operations of (i) adding particulate drug, liquefied HFA 134a and/or HFA 227 propellant and, if used, other non-HFA 134a/HFA 227-propellant component or components into a vessel, wherein said one or more powered, submersed ultrasonic probes are located in said vessel.

4. A method according to claim 3, wherein the mixture is being mixed in said vessel.

5. A method according to claim 1, wherein the steps of providing and subjecting (steps a and b) comprise the operations of (i) adding particulate drug, liquefied HFA 134a and/or HFA 227 propellant and, if used, other non-HFA 134a/HFA 227-propellant component or components into a vessel; (ii) circulating the mixture out of the vessel and back into the vessel through a re-circulation loop; and wherein said one or more powered, submersed ultrasonic probes are located in the re-circulation loop or in the vessel or, if applicable both.

6. A method according to claim 1, wherein the method includes subjecting said mixture to two or more powered, submersed ultrasonic probes.

7. A method according to claim 1, wherein the step of filling (c) comprises the operations of (i) transferring the treated mixture to a second vessel in a filling line; (ii) circulating the treated mixture out of the second vessel and back into the second vessel through a second re-circulation loop in the filling line; and (iii) delivering from the filling line via a filling head a metered aliquot of treated mixture into the aerosol container.

8. A method according to claim 7, wherein the step of filling (step c) comprises subjecting said treated mixture to one or more powered ultrasonic probes, while agitating said treated mixture, said one or more probes being submersed in said treated mixture and located in the re-circulation loop of the filling line or in the filling vessel of the filling line or, if applicable, both.

9. A method according to claim 1, wherein in step of providing (step a), the amounts of particulate drug, liquefied HFA 134a and/or HFA 227, and, if used, other component(s) are equal to that amount deemed required for selected, targeted number of canisters to be filled.

10. A method according to claim 1, wherein in the step of providing (step a) the amount of particulate drug is equal to that amount deemed required for selected, targeted number of canisters to be filled, and wherein the amount of liquefied HFA 134a and/or HFA 227 propellant is less than that amount deemed required for selected, targeted number of canisters to be filled and, if used, other component(s) are equal to or less than that amount deemed required for selected, targeted number of canisters to be filled; and wherein the method comprises a further step prior to the step of filling (step c) and after the steps of providing and subjecting (step a and b), said further step comprising combining liquefied HFA 134a and/or HFA 227 propellant and, if applicable, other component(s) with the treated mixture such that amount of propellant and other component(s), if used, are equal to those amount(s) deemed required for selected, targeted number of canisters to be filled.

11. A method according to claim 1, wherein the drug is selected from group consisting of an anti-inflammatory, anti-allergic, anti-asthmatic, anti-histamine, anti-cholinergic agent, anorectic, anti-depressant, anti-hypertensive agents anti-neoplastic agent, anti-tussive, anti-anginal, anti-infective, anti-migraine drug, anti-peptic, dopaminergic agent, analgesic, beta-adrenergic blocking agent, cardiovascular drug, hypoglaecemic, immunomodulator, lung surfactant, prostaglandin, sympathomimetic, tranquilizer, steroid, vitamin, sex hormone, vaccine, therapeutic sense or anti-sense nucleic acid, other therapeutic protein and other therapeutic peptide, and mixtures thereof.

12. A method according to claim 1, wherein the valve is a metered dose valve.

13. A medicinal dispenser comprising a medicinal aerosol canister manufactured according to claim 1.

14. A dispenser according to claim 13, wherein the dispenser is a metered dose medicinal dispenser.

15. A dispenser according to claim 14, wherein the metered dose medicinal dispenser is a pressurized metered dose inhaler.

16. A method according to claim 1, wherein the targeted number of canisters to be filled is 2000 or more.

17. A method according to claim 1, wherein the targeted number of canisters to be filled is 5000 or more.

18. A method according to claim 1, wherein said one or more powered, submersed ultrasonic probes are powered non-continuously.

19. A method according to claim 1, wherein one or more powered, submersed ultrasonic probes are elongate.

* * * * *